United States Patent [19]

Kvitash

[11] Patent Number: 4,527,240
[45] Date of Patent: Jul. 2, 1985

[54] BALASCOPY METHOD FOR DETECTING AND RAPIDLY EVALUATING MULTIPLE IMBALANCES WITHIN MULTI-PARAMETRIC SYSTEMS

[76] Inventor: Vadim I. Kvitash, 1775 Seventeenth Ave., San Francisco, Calif. 94122

[21] Appl. No.: 454,196

[22] Filed: Dec. 29, 1982

[51] Int. Cl.$^3$ .................... G06F 15/42; A61B 5/04
[52] U.S. Cl. ..................... 364/415; 128/710; 340/741; 364/582
[58] Field of Search ............... 364/413, 415, 416, 518, 364/550, 551, 552, 582; 128/709, 710, 630; 340/722, 741; 346/33 ME

[56] References Cited

U.S. PATENT DOCUMENTS

| | | | |
|---|---|---|---|
| 3,811,040 | 5/1974 | Weinfurt et al. | 364/582 |
| 3,835,839 | 9/1974 | Brown | 364/415 |
| 4,027,148 | 5/1977 | Rosenthal | 340/741 |
| 4,093,857 | 6/1978 | Lapidus | 364/414 |

Primary Examiner—Joseph Ruggiero
Attorney, Agent, or Firm—David Pressman

[57] ABSTRACT

In a system in which multiple related parameters, such as blood chemistry data, are to be evaluated, such evaluation is facilitated by converting the data into specially normalized units as a percentage on a scale depicting the maximum and minimum empirical values for such parameter. Then a normal relationship between pairs of such data (FIG. 1—N) is provided and compared with measured relationships between corresponding pairs of data (FIG. 1—CN to FN) and quantitative and qualitative evaluations are made. Also the complete set of data for such a system is plotted on respective radial axes in such normalized units on a circular coordinate system with the respective maximum and minimum for each parameter being marked on its radius (FIG. 2). The maxima and minima are interconnected to form two closed lines (22), thereby to provide an annulus representing the normal range. Then measured parameters for various entitities are similarly plotted and compared with the normal annulus or known abnormal annuli (FIGS. 3 to 7). Also circular point diagrams are provided, with points on a circular path representing respective parameters and respective pairs of points being connected in cases where a normal quantitative relationship exists (FIG. 8A) or where a specified type of qualitative abnormal relationship exists (FIGS. 8B to 8F), thereby to depict more readily the condition of the system. The data or parameters may be plotted with the aid of an EDP system (FIG. 9).

10 Claims, 15 Drawing Figures

TOTAL SERIUM PROTEIN (P)
AND SERIUM ALBUMIN (A)
LEVEL IN BU

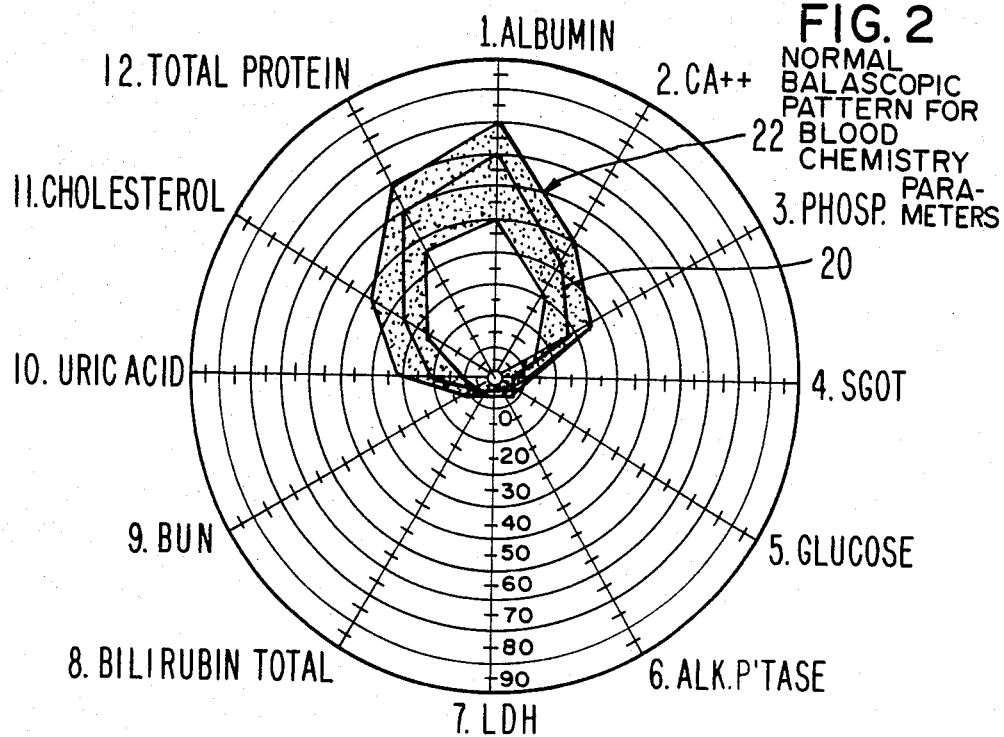
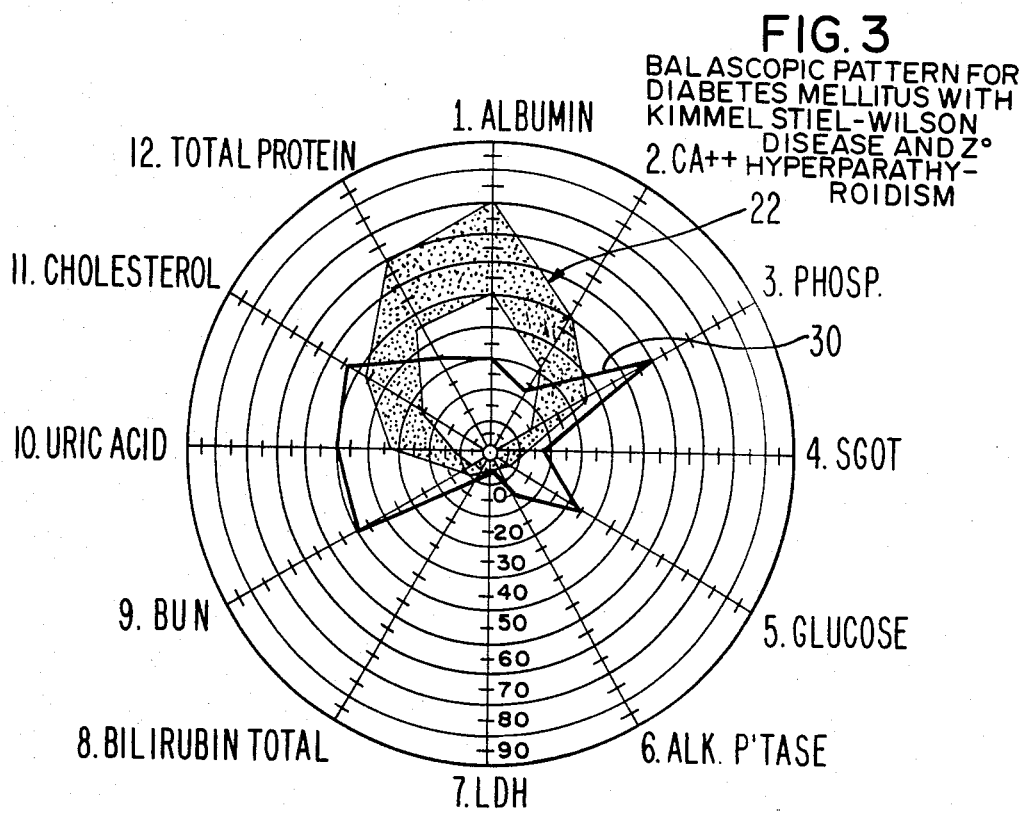

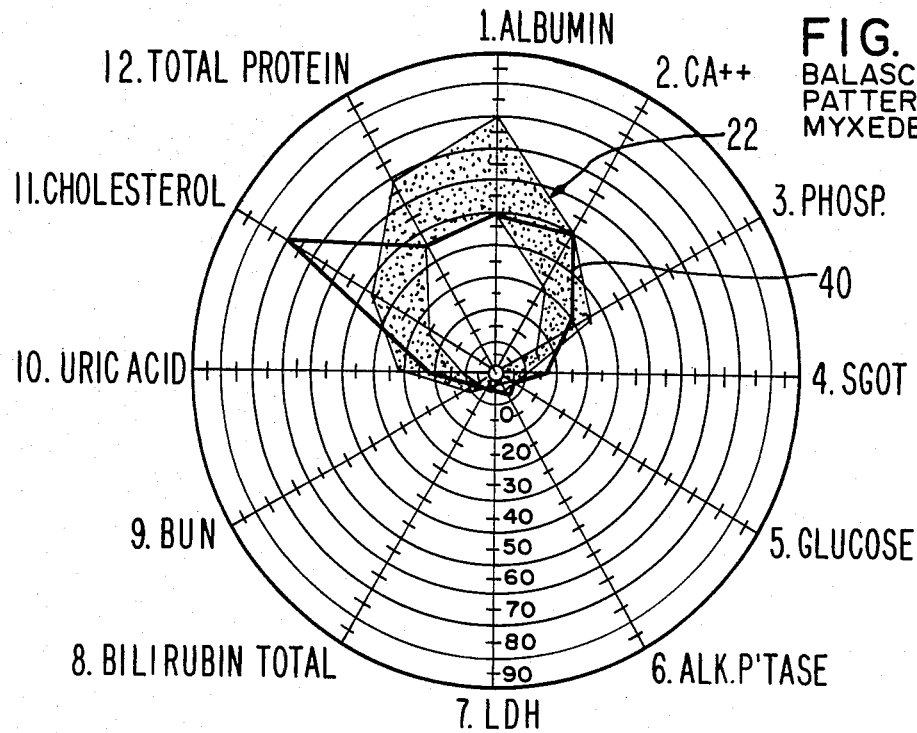
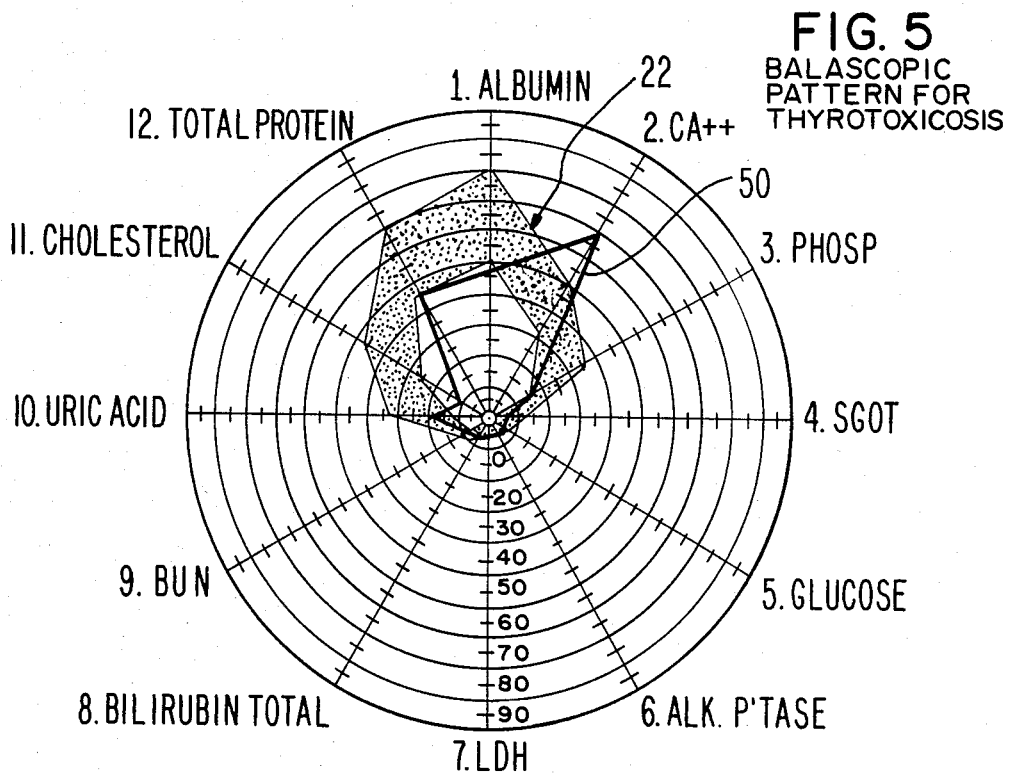

BALASCOPIC PATTERN FOR
MYOCARDIAL INFARCT (MI)

| BU | 64 | 35 | 26 | 66 | 14 | 6 | 13 | 4 | 9 | 39 | 37 | 57 | PARAMETER |
|---|---|---|---|---|---|---|---|---|---|---|---|---|---|
| ACT. VAL. (Mg/dl OR v/l) | 4.2 | 8.8 | 3.6 | 330 | 183 | 84 | 665 | .6 | 15 | 8.4 | 218 | 7.1 | |
| | 1 | 2 | 3 | 4 | 5 | 6 | 7 | 8 | 9 | 10 | 11 | 12 | |
| | | N | N | CI 96% | CN 6% | N | CN 9% | N | N | CN 22% | N | N | 1 |
| | | | N | NI | CN 22% | CN 3% | CN 27% | N | N | CI 20% | NI | N | 2 |
| | | | | FI 12% | N | N | CN | N | N | NI | N | N | 3 |
| | | | | | FI 49% | FN | FN 51% | FN 59% | FI 53% | NI | NI | CI 80% | 4 |
| | | | | | | FN 3% | N | FN | NI | N | N | N | 5 |
| | | | | | | | FN 5% | N | N | FN 4% | N | N | 6 |
| | | | | | | | | FN 4% | NI | N | N | CN 4% | 7 |
| | | | | | | | | | N | FN 4% | N | N | 8 |
| | | | | | | | | | | FN 4% | N | N | 9 |
| | | | | | | | | | | | NI | CN 22% | 10 |
| | | | | | | | | | | | | N | 11 |

IMBALANCE

FIG. 7
PARAMETRIC QUALITATIVE RELATIONSHIPS – MI OF FIG. 6

LEDGEND:
N = NORMAL
CN = CLOSER THAN NORMAL
FN = FARTHER THAN NORMAL
NI = NORMAL & INVERTED
CI = CLOSER & INVERTED
FI = FARTHER & INVERTED

N: 50%

N·I: 12%

CN: 14%  MEAN = 14  CV = 70%

CI: 5%
MEAN = 65
CV = 61%

FN: 14%  MEAN = 21  CV = 125%

FI: 6%
MEAN = 30
CV = 83%

FIG. 8 — CIRCULAR POINT AND LINE PLOTS FOR EACH PARAMETRIC RELATIONSHIP OF MI OF FIG. 6

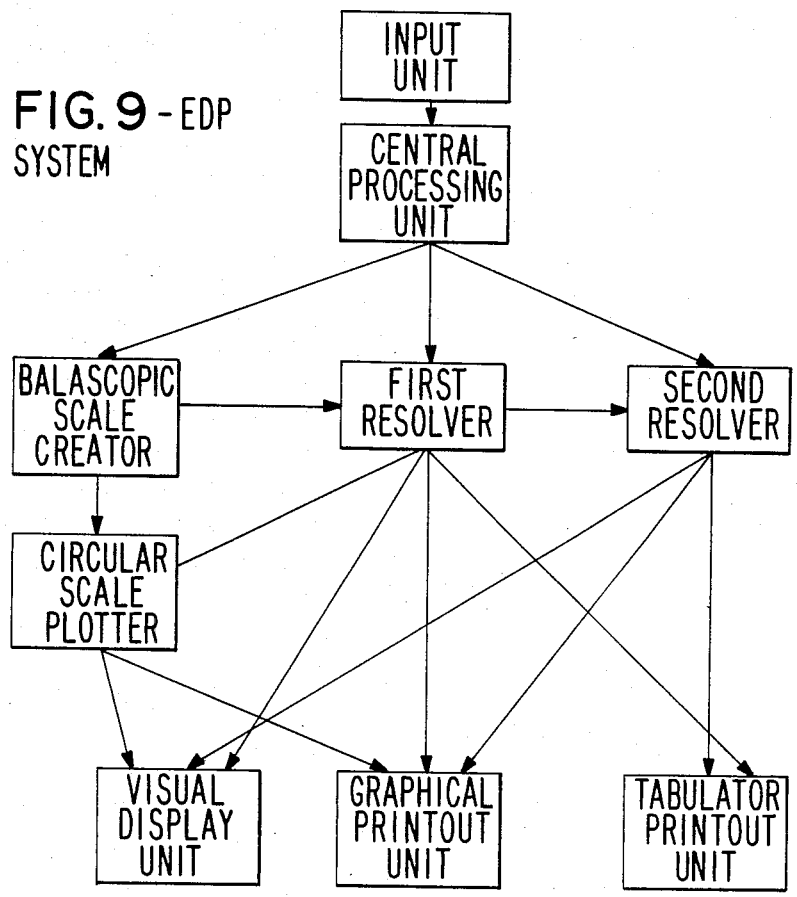
FIG. 9 - EDP SYSTEM

_4,527,240_

BALASCOPY METHOD FOR DETECTING AND RAPIDLY EVALUATING MULTIPLE IMBALANCES WITHIN MULTI-PARAMETRIC SYSTEMS

BACKGROUND

1. Field of Invention

The present invention relates to the detection and evaluation of multiple imbalances within multi-parametric systems, particularly to the employment of graphic means for performing such detections and evaluations. It is particularly useful in the field of medicine for the diagnosis and follow-up treatment of diseases. It may be used in many other fields for evaluating, diagnosing, predicting, analyzing, describing behavior, change of behavior, etc., where multiple parameters in a related system are involved.

2. Description of Prior Art

In medicine, for optimal care and therapy, quantitative as well as qualitative judgments of the degrees of abnormalities should be made when diagnosing patients. Previous studies have suggested that an analysis of combinations of laboratory data of a patient may be of greater aid in understanding the patient's condition than an analysis of individual items of data per se.

Heretofore one scientific method of diagnosing diseases from laboratory data has used a statistical analysis of deviations of a patient's data from a normal range. The results obtained were arranged in the form of a circular coordinate system which employed radial axes calibrated according to the patient's laboratory parameters, with standard deviations of each parameter plotted on the respective axes. Following this, a pattern was created by interconnecting adjacent points on the axes. Diagnosis was performed by comparing the obtained pattern of an individual patient with reference patterns typical for certain diseases. J. H. Siegel, "Relations Between Circulatory and Metabolic Changes in Sepsis," 32 Ann.Rev.Med. (Annual Reviews, Inc. 1981) 175-194; also see the "Patient Data System," General Electric Medical Systems (adv't.), Critical Care Medicine, Jan/Feb 1976.

While useful, these methods did not provide sufficient information for one to detect pathology with normal data and did not reveal qualitative and quantitative types of imbalances between parameters.

Another method has been suggested in an attempt to overcome these difficulties. This method was similar to the previous ones: a circular type presentation of parameters on radial axes was provided with values plotted on the radial axes, but expressed as a percentage of normal values, rather than by standard deviations. S. Nazari et al., "A Multivariable Pattern for Nutritional Assessment," 4 J. Parenteral and Enteral Nutrition 499, 1980.

This method provided more distinguishable patterns than the previous one because the percentage scale was more sensitive than the standard deviation scale. Nevertheless this method still did not provide sufficient information for one to obtain quantative and qualitative types of imbalances between parameters and did not reveal any multiple imbalances which were present within the system.

OBJECTS

Accordingly one object of the invention is to obviate the disadvantages inherent in existing modes of analyzing, diagnosing, and evaluating medical and other data. Another object is to provide a new method of evaluation based on quantitatively and qualitatively-determined types of imbalances between measured parameters in a medical or other system. Further objects and advantages will become apparent from a consideration of the ensuing description and accompanying drawings.

DRAWINGS

FIG. 2 is a circular diagram of a normal pattern of blood chemistry parameters, made according to a method of the present invention.

FIGS. 3 to 6 are circular diagrams of abnormal blood chemistry patterns typical for various diseases, plotted according to the invention and with normal pattern ranges being superimposed thereon.

FIG. 7 is a table showing the data for the parameter set of FIG. 6, compiled according to the invention.

FIG. 8, parts A to F, shows dot and line diagrams designed to vivify parametric relationships according to the invention.

FIG. 9 is a block diagram of an EDP system which may be employed in the practice of the invention.

DESCRIPTION

Medical Use of Invention

Generally, laboratory data or measured parameters of a patient are used to make and confirm a diagnosis and to monitor the course of treatment. In a basic aspect of the present invention, each measured parameter of a patient is noted and is made far more useful and meaningful by expressing it as a percentage between the minimum and maximum empirical values of said parameter.

For example, the empirically existing maximum of the total serum protein in vivo comprises 11.0 milligrams (mg) of protein per tenth liter (deciliter—dl) of blood, and the minimum is 2.0 mg/dl. The range between these values is thus $11.0 - 2.0 = 9.0$ mg/dl. This range is then converted into special normalized units on a scale of 100, such that each normalized unit will correspond to $100/9 = 11.1$ actual units (in mg/dl). A patient's measured total serum protein value may be thus converted to normalized units by subtracting the minimum actual value from the patient's actual value and then multiplying the result by 11.1 or by 100/9.

EXAMPLE 1

For example, if a patient's measured total serum protein is 7.3 mg/dl, this value is made the minuend, the minimum empirical value (2.0 mg/dl), is made the subtrahend, and the difference, 5.3 mg/dl, is determined. This difference (5.3 mg/dl) is then multiplied by the normalized unit value, 11.1, to provide a special normalized value according to the invention, which is 58.9 units.

I have designated these special normalized units (regardless of the parameter represented) by the term Balascopic ™ units [bala>balanced, and scopic>see] and they will be so referred to hereinafter for ease of discussion. I have designated my process Balascopy ™.

Figure 1:
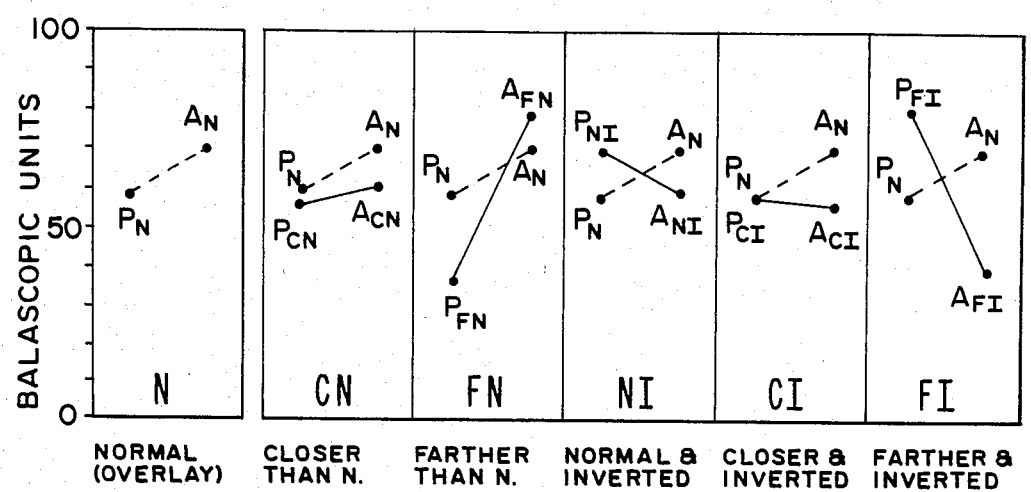
FIG. 1 is a diagram illustrating various types of imbalances in two blood chemistry parameters according to a method of the present invention.

FIG. 1—Use of Balascopic Units to Portray Relationships

FIG. 1 shows how Balascopic units can be used to express relationships between measured parameters of a patient in more meaningful terms.

In FIG. 1 the vertical scale is calibrated in Balascopic units (BU) from 0 to 100, with 0 BU corresponding to the existing empirical minimum and 100 BU corresponding to the existing empirical maximum of both total serum protein and serum albumin of a patient. The first (leftmost) block of this diagram (labeled Normal and N) shows how Balascopic units can be used to represent a normal relationship between these two blood parameters. In this block, point $P_N$ represents a normal value of total serum protein in a patient. The absolute value of Example 1 when converted from mg/dl—not indicated—to Balascopic units, gives 58.9 or 59 BU, as explained.

Assume further that the normal patient's serum albumin is measured in an absolute measurement (not indicated) and when converted to Balascopic units (according to the above-described method), is 70 BU. This parameter is indicated at point $A_N$.

A broken line is drawn to connect points $P_N$ and $A_N$; this line indicates the normal relationship between these two parameters. A normal differential (sometimes called "gradient") between total serum protein ($P_N$) and serum albumin ($A_N$) is thus equal to 70 BU $-$ 59 BU $= 11$ BU. Preferably block N is made of transparent material so that it can be superimposed over any other block in FIG. 1.

In FIG. 1, the second block from the left, CN, illustrates a deviation from the normal relationship between total serum protein and serum albumin. In this case the values are Closer than Normal (CN); this closer than normal relationship is sometimes called an "integrated" relationship. According to the previous procedure, the two values are measured, converted to BU, and the resultant points are connected. The resultant differential between them is assumed equal to 5 BU, i.e., less than the normal differential (Block N) of 11 BU.

Since the two values P and A in blocks N and CN are plotted the same distance apart, the gradients of their interconnection lines can be easily compared by a superimposition of the normal gradient upon the actual measured gradient in block CN. The abnormality of the patient in block CN can easily be seen by the reduced slope of the solid gradient line $P_{CN}$—$A_{CN}$ in this block when compared with the normal gradient (broken line $P_N$—$A_N$).

Similarly a type of imbalance where the two parameters are too far apart in shown in the next block, FN (Further than Normal). Here the Balascopic differential is equal to 40 BU, which is farther than the normal 11 BU differential. This "FN" (sometimes called "disintegrated") relationship can easily be seen by the increased slope of the interconnection line $P_{FN}$—$A_{FN}$, especially when compared with the superimposed normal gradient (broken line $P_N$—$A_N$) superimposed thereover.

In the next block (NI) line $P_{NI}$—$A_{NI}$ has a normal Balascopic gradient of 11 BU, but the mutual positions of the two points are inverted from normal. This type of relationship is calld Normal Inverted (NI) and also is vividly demarcated by the superimposed broken line $P_N$—$A_N$.

In the next block CI (Closer and Inverted) (sometimes called "integrated" and inverted), line $P_{CI}$—$A_{CI}$ represents a closer than normal and inverted relationship with a Balascopic gradient of 10 BU. Compare this line with the normal broken line $P_N$—$A_N$. In the last block, FI, a Farther than Normal and at the same time inverted relationship is shown by the line $P_{FI}$—$A_{FI}$. This farther than normal and inverted (sometimes called "disintegrated" and inverted) relationship is also vividly demarcated by the superimposed normal broken line $P_N$—$A_N$.

As will be recognized by those skilled in the art, the above method reveals five new definitive and qualitative types of imbalances between blood chemistry parameters that can be established. This method can also be used for any given pair of parameters in a system of related parametric quantities. Each of the above imbalances can be quantitatively estimated by the degree of imbalance in percent.

FIG. 2—Simultaneous Comparison of Several Parameters for Normal Patient

The relationships between many parameters in a system or related parameters can be represented simultaneously by the method illustrated by the diagram of FIG. 2. FIG. 2 shows a circular coordinate system having twelve radial lines corresponding to twelve standard blood chemistry parameters, 1. albumin, 2. $Ca^{++}$ (Calcium ions), 3. phosphorus, 4. SGOT (serum glutamic oxytransaminase), 5. glucose, 6. alkaline phosphatase (alk. p'tase), 7. LDH (lactic dehydrogenose), 8. bilirubin total, 9. BUN (blood urea nitrogen), 10. uric acid, 11. cholesterol, and 12. total protein. The reference or normal range for these parameters are plotted in normalized or Balascopic units (BU) on the respective axes in the manner aforedescribed. The mean values of these parameters are then interconnected to form a closed or endless line 20.

The shaded ring-shaped or annular area 22 in FIG. 2 shows the normal range for a healthy population chosen by conventional statistical methods. Area 22 is drawn by plotting the normal lowest and highest values for each parameter on its radial axis, and then interconnecting the lowest points and the highest points to form two closed lines (similar to line 22) and shading the area between these lines. Note that the parameters connected by line 20 all fall within the normal range. In order to simplify the visual comparison and present it in a more obvious way, the radial axes on the circular diagrams of FIGS. 2-6 are arranged in the specific order indicated (rather than the standard sequence of a laboratory test routine) so that the boundaries limiting the normal range will define the substantially annular pattern shown. If the axes were arranged in an order corresponding to the sequence of a standard laboratory test routine, the pattern of the normal range would have been too complicated for comparison and too difficult to employ as an effective and in diagnosis.

FIGS. 3 to 6—Simultaneous Comparison for Various Pathological Conditions

FIGS. 3 to 6 are similar circular diagrams depicting abnormal patterns of blood chemistry typical for the various diseases indicated. In each of these figures, the corresponding normal (shaded) range pattern 22 is superimposed on the patient's annular blood chemistry plotted line.

In FIG. 3, the blood chemistry for a patient with diabetes mellitus with Kimmelstiel-Wilson disease and secondary hyperparathyroidism is plotted as line 30.

In FIG. 4, the blood chemistry for a patient with myxedema is plotted.

In FIG. 5, the blood chemistry for a patient with thyrotoxicosis is plotted.

It can be seen that the use of a circular diagram with the normal range for the blood chemistry parameters plotted as a shaded ring and the patient's parameters plotted thereover or thereunder by a solid line greatly facilitates, strengthens, and improves diagnosis, especially when prototype patterns for typical diseases (such as shown in FIGS. 3 to 6) are superimposed on the diagram, either with (not shown), or in lieu of the normal annular shaded area of FIG. 2.

EXAMPLE 2

FIG. 7

It is now possible and desirable to obtain a full set of the existing relationships between all parameters of blood chemistry expressed in terms of Balascopic differences or gradients. Skipping FIG. 6 temporarily, this can be seen in FIG. 7, where the blood chemistry data from a recently measured patient with a myocardial infarction (MI) and their corresponding values in Balascopic units (BU) are presented and taken from Table 1 below.

TABLE 1

| BLOOD CHEMISTRY FROM PATIENT WITH MI | | | | |
|---|---|---|---|---|
| Parameter Nr. | Parameter | Actual Value | Units | BU |
| 1 | Albumin | 4.2 | mg/dl | 64 |
| 2 | CA++ | 8.8 | mg/dl | 35 |
| 3 | Phosphorous | 3.6 | mg/dl | 26 |
| 4 | SGOT | 330 | U/l | 66 |
| 5 | Glucose | 183 | mg/dl | 14 |
| 6 | Alk. P'tase | 84 | U/l | 6 |
| 7 | LDH | 665 | U/l | 13 |
| 8 | T. Bilirubin | .6 | mg/dl | 4 |
| 9 | BUN | 15 | mg/dl | 9 |
| 10 | Uric Acid | 84 | mg/dl | 39 |
| 11 | Cholesterol | 218 | mg/dl | 37 |
| 12 | Total Protein | 7.1 | mg/dl | 57 |

By way of example, consider the first line of Table 1 which shows how this patient's albumin, measured as 4.2 mg/dl, is converted to Balascopic units (BU). The lowest value of albumin measured in a a living patient is 1.0 mg/dl. The highest value is 6.0 mg/dl. According to the principle of Balascopy, the difference between these maximum and minimum is taken to be 100 BU. To convert the patient's actual value of 4.2 mg/dl into BU, subtract the existing minimum (1.0) from the actual value (4.2) multiply the result by 100 divide by the difference betwen the existing maximum and the existing minimum (5.0) to obtain the value indicated in the rightmost column, 64 BU.

The other blood parameters for this patient have also been processed in this manner to obtain the data in the "BU" column. This patient's blood chemistry parameters are also presented as line 60 in the radial chart of FIG. 6, with the shaded area 22 again representing the normal range and line 60 representing the patient's parameter's in BU, superimposed over the "normal" annulus.

Figure 6:
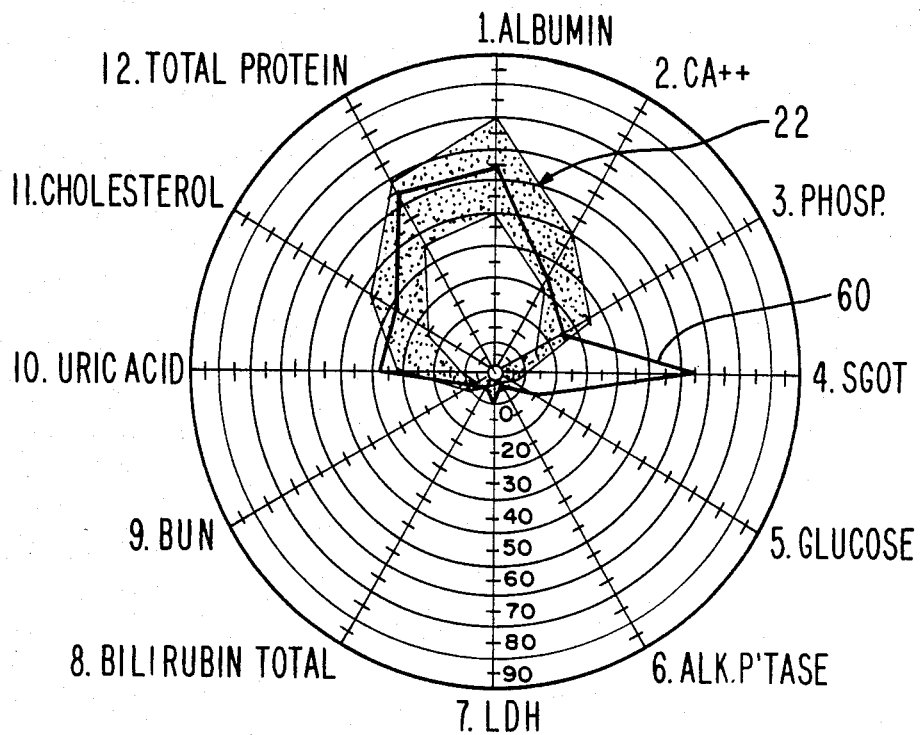

Note that Table 1 above presents relatively little readily-understandable information and is difficult to analyze or evaluate, either initially, or on a follow-up monitoring, while the chart of FIG. 6 presentes a readily-identifiable portrayal of this patient's pathology.

FIG. 7—Parametric Quantitative, and Qualitative Relationships—MI of FIG. 6

While FIG. 6 vividly depicts the patient's quantitative relationships, the chart of FIG. 7 shows the entire spectrum of all existing parametric relationships in quantitative as well as qualitative terms, and also indicates the actual and Balascopic units for each parameter. For example in the parameter row (third row down, just above double line) parameter 1 has an actual value (second row down) of 4.2 mg/dl and a value in BU (top row) of 64 units. The parameters are also indicated by number in the rightmost column, to the right of the double line.

The qualitative relationship of parameter 1 (rightmost column) with parameter 10 (third row down) is indicated to be closer than normal by the legend "CN" in the block at the intersection of parameters 1 and 10 and this relationship quantitatively is a 22 percent imbalance (same block).

These qualitative and quantitative relationships can be determined as follows: The Balascopic difference between parameter 1 (64 BU) and parameter 10 (39 BU) is 64−39=25 BU. The average Balascopic difference between these two parameters for the healthy population is 48.2 BU, with a standard deviation (SD) of 8.1 BU. Thus the Balascopic difference for a normal relationship (about 95% of the population) should lie between the limits of the average value ("X")±2 SD. Since X is 48.2 BU, this range extends for 48.2±(2×8.1) BU or 32.0 to 64 BU. This means that any value of Balascopic difference for a patient's parameters 1 and 10 between 32.0 and 64.4 BU can be considered a normal relationship.

In the present example, the Balascopic difference is only 25 BU, which is less than 32.0 BU and therefore is an imbalance type of relationship, a CN (Closer than Normal) type because the difference (25 BU) is less than the normal difference.

To evaluate the quantitative degree of closeness, consider the range between the lower limit of the normal difference (32 BU) and the maximum closeness (0 BU) as 100% and determine the degree of actual closeness in percent.

In the present case the lower limit of normal difference (32 BU) less the actual difference (25 BU) divided by the lower limit (32) times 100=22 percent, as indicated in FIG. 7 in the block at the intersection of parameters 1 and 10.

To take another example, the Balascopic gradient between parameter 4 (66 BU) and parameter 7 (13 BU) is 53 BU. The average Balascopic gradient between parameters 4 and 7 for a healthy population is 1.3 BU, with the SD being 1.4 BU. Thus the Balascopic gradient for a normal relationship should lie between the limits of 1.3±2.8 BU, or −1.8 BU to +4.5 BU. However, because negative values are meaningless, the lower limit is raised to zero and the normal range is considered from 0 to 4.5 BU. In the present case, the differential of 53 BU far exceeds the normal range, i.e., is a farther than normal (FN) type of imbalance. The degree of imbalance or farness is equal to the given differential less the upper limit of the normal differential times 100% divided by the difference between 100 BU and the upper limit of the normal differential or 48.5 BU×100%−95.5 BU=51%.

The formulae above used are valid for all of the abnormal qualitative relationships indicated in FIG. 1 (CN, FN, CI, and FI).

The following Table 2 is a statistical analysis of the data in Table 1 and FIG. 7. This table shows, for the 66 existing pairs of relationships of the 12 blood parameters used, the actual number of occurrences of each type of relationship, the percentage of the total for each type of relationship, the statistical mean, in BU, of each type of relationship, and the statistical coefficient of variation for each relationship.

TABLE 2

Statistical Analysis of Relationships of FIG. 7 and Table 1

| Type of Relationship | Occurrences | Percent of Total Occurrences | Mean in BU | Coefficient of Variation |
| --- | --- | --- | --- | --- |
| N | 33 | 50 | — | — |
| NI | 8 | 12 | — | — |
| CN | 9 | 14 | 13.55 | 70 |
| FN | 10 | 15 | 21.00 | 125 |
| CI | 3 | 5 | 65.33 | 61 |
| FI | 3 | 4 | 29.75 | 83 |

As will be appreciated by those skilled in the art it is difficult to draw a conclusion from data presented in the above tabulation, but by processing the data and presenting it in the form of the analytical graphs according to the invention with superimposed normal or known condition range values, a far clearer picture of pathology is readily presented.

FIG. 8—Circular Point and Line Diagrams—MI of FIGS. 6 & 7

FIG. 8 presents another method of graphically portraying the relationships and more vividly indicating the degree of abnormality. FIG. 8 is divided into six parts, FIGS. 8A to 8F, respectively showing the six types of metabolic relationships (N, CN, FN, NI, CI, and FI), as disussed for the patient with the myocardial infarct whose data are presented in the foregoing tables and in FIGS. 6 and 7.

Each part of FIG. 8 has 12 dots, numbered 1 to 12, spaced evenly in a circular configuration, each dot representing one of the 12 blood chemistry parameters aforediscussed. In each part of FIG. 8, every pair of parameters which have the metabolic relationship specified by the heading of the part is indicated by a line interconnecting the pair of dots representing the parameters which have such a metabolic relationship. Thus in FIG. 8A, the dots for every pair relationship which have a normal relationship, i.e., the relative values of the parameters are in the normal relationship range, are interconnected by a line. In the patient under consideration, the relative values for the following parameters are in the normal range and hence the following pairs of dots are joined in FIG. 8A: 1-2, 1-3, 1-6, 1-8, 1-9, 1-11, 1-12, 2-3, 2-8, 2-9, 2-12, 3-5, 3-6, 3-8, 3-9, 3-11, 3-12, 5-7, 5-10, 5-11, 5-12, 6-8, 6-9, 6-11, 6-12, 7-10, 7-11, 8-9, 8-11, 8-12, 9-11, 9-12, and 11-12.

Figure 8A:
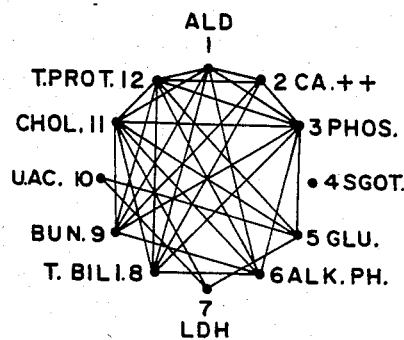

Since 50% of all existing pairs of parameters are joined in FIG. 8A, this is indicated by the legend "N: 50%" meaning that 50% of the parametric relationships for this patient are normal. Obviously the more lines that are present in a "normal" diagram (FIG. 8A), the better the patient's blood chemistry condition.

Figure 8B:
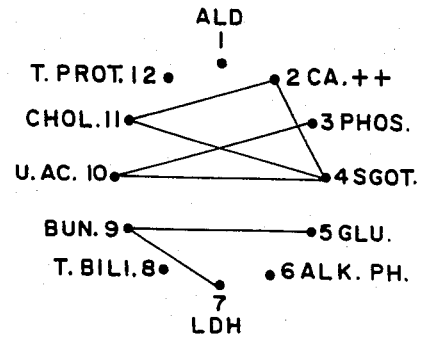
Figure 8C:
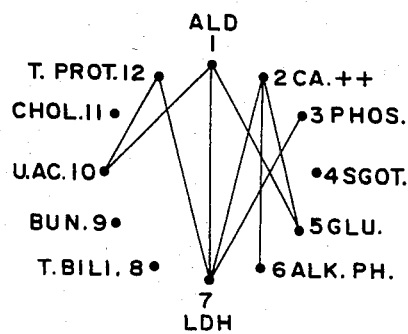
Figure 8D:
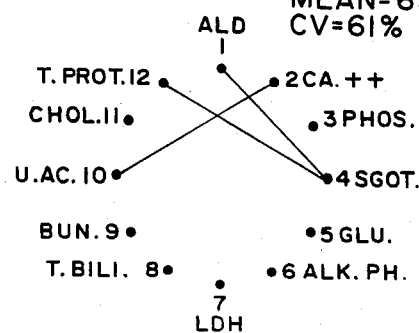
Figure 8E:
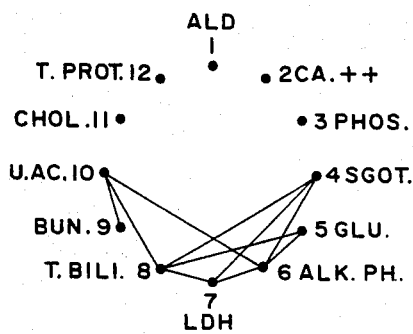
Figure 8F:
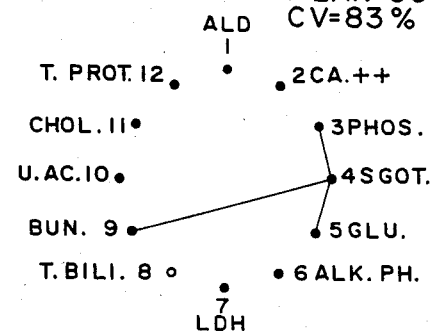

In FIG. 8B, on the other hand, lines are shown for only the parametric relationships which are abnormal in the normal but inverted (NI) manner. Since this is a pathalogical condition, obviously the more lines which are present in FIG. 8B (as well as FIGS. 8C to 8F), the worse the patient's condition. As indicated in FIG. 8B, 12% of the patient's blood chemistry parametric relationships are normal-inverted (NI).

The remaining four sections, C, D, E, and F, of FIG. 8 represent the CN, CI, FN, and FI abnormal relationships and the percentages of each of these abnormal of these abnormal relationships is indicated. In each of these sections, the mean degree of abnormality (in BU) of the represented abnormal parameter is also indicated, as is the statistical coefficient of variation (CV) of such abnormal parameters. (No mean or CV is indicated in FIGS. 8A or 8B because these sections represent parametric relationships with quantitatively normal values).

It will be appreciated that the charts of FIG. 8 will present significantly more assimilable information to a trained person than numerical data alone, or prior art charts. Also follow up evaluation is greatly facilitated by comparing charts for a patient at sequential stages of a disease.

FIG. 9—Use of EDP System

Although foregoing charts and tables of the invention can be assembled and plotted manually, preferably they should be done by an electronic data processing system to eliminate manual labor, eliminate errors, and speed evaluation. A system such as that shown in FIG. 9 would be suitable. The system comprises an input unit (IU), such as a keyboard, cardreader, or the like, a central processing unit (CPU) which includes a Read And write Memory (RAM) and software; a Balascopic scale creater (BSC), which serves to convert laboratory data from standard units to Balascopic units (BU); a first resolver units (R1), which determines quantitative criteria for normal relationships and for each type of abnormal relationship; a second resolving unit (R2) which develops quantitative parameters of the degree of imbalance for each type of imbalance; a circular scale plotter (CSP) which creates circular diagrams with radial axes corresponding to the respective laboratory data parameters and which plots the data in Balascopic or any other units on said axes; a visual display unit (VDU); and an optional graphical printout unit (GPU) and tabulator printout unit (TPU). The units preferably are connected as indicated but alternatively, for versatility, all units can be connected directly to and from the CPU. All of the units of FIG. 9 are available in the art and the programming can be readily done by an experienced programmer.

The system of FIG. 9 operates in the following manner: Laboratory data for a patient are inputed from the IU to the CPU and stored in its RAM. Then, under program control, the data are sent to the BSC which converts them into BU and supplies the converted data to the CSP for creating circular diagrams with data plotted in BU on the proper axes. (Alternatively the data from the BSC can be fed to R1 and from R1 to the CPU, CSP, VD, GPU, or TPU.). The output of R1 is connected to R2, the latter supplying output information to the the CPU and to the VDU, GPU, and TPU.)

The above described system allows one to obtain new and useful presentations of information which can be used for diagnosis, monitoring, and control of treatment of various diseases.

While the above description contains many specificities, they should not be construed as limitations of the scope of the invention, but rather as examples of several preferred embodiments thereof. Various other embodiments and ramifications are possible within its scope. For example instead of blood chemistry, data other types of medical data, in any multi-parametric system, such hematological data, neurological data, dietic data, coronary data, etc., cal be converted to BU and charted. In addition to medicine, the invention can be used in other field where multiple related parameters are found, such as corporate security evaluation, competitive sports analysis and prediction, etc. Accordingly the full scope of the invention should be determined not be the examples given, but by the appended claims and their legal equivalents.

I claim:

1. A method of evaluating data in a multi-parametric system, comprising the steps of:
   (a) obtaining a plurality of parametric data of such system;
   (b) converting each datum obtained to a specially-normalized unit value equal to a percentage based upon the value of each parametric datum within the range between two existing and previously-determined extreme values of said parametric datum;
   (c) providing a circular coordinate scale having radial axes corresponding to said respective parametric data of such system, each axis being identically calibrated in said specially-normalized unit values;
   (d) plotting said specially-normalized unit values of said data as points on their respective axes of said circular coordinate scale;
   (d) creating a pattern by interconnecting points on adjacent ones of said radial axes to form a closed configuration pattern; and
   (e) evaluating said multi-parametric system by comparing said closed configuration pattern with at least one reference pattern plotted on a similar circular coordinate scale and representative of a known state in said system.

2. The method of claim 1 wherein said radial axes are calibrated and arranged such that the boundaries limiting a normal range define substantially an annular pattern.

3. The method of claim 1 wherein said reference pattern is formed on a scale identical to that of said scale in which the normalized units are plotted and said evaluating comprises overlaying said normal pattern upon said pattern from obtained data.

4. The method of claim 1 wherein said parametric data are medical laboratory data of a patient and said converting of each datum to a specially-normalized unit value comprises the determination of the percentage of the value of each datum between previously known extreme values of such medical laboratory data.

5. The method of claim 4 wherein said medical laboratory data are data selected from the group consisting of the following blood chemistry parameters: albumin, calcium ions, phosporus, serum glutamic oxytransaminase, glucose, alkaline phosphatase, lactic dehydrogenose, bilirubin total, blood urea nitrogen, uric acid, cholesterol, and total protein.

6. A method of analyzing and evaluating a multi-parametric system, comprising the steps of:
   (a) obtaining a plurality of parametric data of such system;
   (b) converting each datum obtained into normalized units by calculating a percentage based upon the value of each parametric datum within the range between two existing extreme values of said parametric datum;
   (c) comparing all possible combination pairs of said normalized unit values to obtain a quantitative value for every possible pair of said normalized unit values;
   (d) comparing the resultant quantitative combination pair values of step (c) with corresponding known and normal quantitative combination pair values to obtain a qualitative relationship for each combinatory pair,
   (e) comparing each quantitative pair value of step (c) to a statistical average quantitative pair value to obtain differential deviation of each quantitative pair value, and
   (f) analyzing said system by comparing said qualitative relationships and said differential deviations with at least one reference set of qualitative relationships and differential deviations for a known condition in said system.

7. The method of claim 6 wherein said related parameters are medical laboratory data of a patient and said analyzing comprises the diagnosis of disease in such patient by comparing said qualitative relationships and differential deviations with those for a known disease condition.

8. The method of claim 6 wherein said analyzing of said system comprises the plotting of a diagram in which each of said parameters is assigned a point at a respective location on said diagram and all pairs of points on said diagram which represent a respective pair of parameters which have a qualitative relationship which falls within of a predetermined value range are interconnected.

9. The method of claim 6 wherein said analyzing of said system comprises the plotting of a diagram in which each of said parameters is assigned a point at a respective location on said diagram and all pairs of points on said diagram which represent a respective pair of parameters which have a qualitative relationship which falls outside of a predetermined value range are interconnected.

10. A system for the diagnosis, monitoring, and control of the effectiveness of treatment, comprising:
   (a) a data input device,
   (b) a central processing unit with a memory, said central processing unit being connected to receive data from said input device,
   (b) a normalized scale creator for converting laboratory data from standard units into normalized units by representing such data as percentage values on a scale representing two existing and extreme values of each datum, said scale creator being connected to said central processing unit;
   (c) a first resolving unit for determining quantitative criteria for normal relationships and for a plurality of types of abnormal relationships as represented by imbalances of said data, said first resolving unit being connected to said central processing unit and said normalized scale creator;
   (d) a second resolving unit for developing quantitative parameters of the degree of imbalance for each type of imbalance of said data, said second resolving unit being connected to said central processing unit and said first resolving unit;
   (e) a circular scale plotter for creating circular diagrams with a plurality of radial axes corresponding to said laboratory data parameters and for plotting said laboratory data in said normalized units on said axes, said circular scale plotter being connected to said normalized scale creator and said first resolving unit;

(e) a visual display unit for selectively displaying data from said circular scale plotter, said first resolving unit, and said second resolving unit, said visual display unit being connected to said last three named units;

(f) a printout unit for printing in graphical form data supplied thereto, said printout unit being connected to said circular scale plotter and said first and second resolving units; and (g) a unit for printing out data in tabular form, said tabular form printout unit being connected to said resolving unit.

* * * * *

UNITED STATES PATENT AND TRADEMARK OFFICE
CERTIFICATE OF CORRECTION

PATENT NO. : 4,527,240

DATED : 1985 July 2

INVENTOR(S) : Kvitash, Vadim I.

It is certified that error appears in the above-identified patent and that said Letters Patent are hereby corrected as shown below:

Title: Change From "Balascopy Method For Detecting And Rapidly Evaluating Multiple Imbalances Within Multi-Parametric Systems" to --Balascopy: Method For Detecting And Rapidly Evaluating Multiple Imbalances Within Multi-Parametric Systems--.

Signed and Sealed this

Twenty-first Day of January 1986

[SEAL]

Attest:

DONALD J. QUIGG

Attesting Officer

Commissioner of Patents and Trademarks